US012735443B2

(12) United States Patent
Jennewein et al.

(10) Patent No.: US 12,735,443 B2
(45) **Date of Patent: *Sep. 15, 2026**

(54) PURIFICATION OF OLIGOSACCHARIDES FROM A FERMENTATION BROTH BY USING FILTRATION

(71) Applicant: Chr. Hansen A/S, Hoersholm (DK)

(72) Inventors: Stefan Jennewein, Bad Honnef (DE); Jan Henrik Krahn, Sankt Augustin (DE); Markus Helfrich, Bad Hoenningen (DE)

(73) Assignee: Chr. Hansen A/S, Hoersholm (DK)

( * ) Notice: Subject to any disclaimer, the term of this patent is extended or adjusted under 35 U.S.C. 154(b) by 726 days.

This patent is subject to a terminal disclaimer.

(21) Appl. No.: 17/612,511

(22) PCT Filed: Apr. 29, 2020

(86) PCT No.: PCT/EP2020/061888

§ 371 (c)(1),
(2) Date: Nov. 18, 2021

(87) PCT Pub. No.: WO2020/233958

PCT Pub. Date: Nov. 26, 2020

(65) Prior Publication Data

US 2022/0251130 A1 Aug. 11, 2022

(30) Foreign Application Priority Data

May 21, 2019 (EP) .................................... 19175716

(51) Int. Cl.

| | |
|---|---|
| ***C07H 1/06*** | (2006.01) |
| ***A23L 33/00*** | (2016.01) |
| ***B01D 61/02*** | (2006.01) |
| ***B01D 61/14*** | (2006.01) |
| ***B01D 61/42*** | (2006.01) |
| ***B01D 61/58*** | (2006.01) |
| ***B01D 69/02*** | (2006.01) |
| ***C08B 37/00*** | (2006.01) |

(52) U.S. Cl.

CPC ................ *C07H 1/06* (2013.01); *A23L 33/40* (2016.08); *B01D 61/025* (2013.01); *B01D 61/026* (2022.08); *B01D 61/027* (2013.01); *B01D 61/145* (2013.01); *B01D 61/146* (2022.08); *B01D 61/147* (2013.01); *B01D 61/422* (2013.01); *B01D 61/58* (2013.01); *B01D 69/02* (2013.01); *C08B 37/0003* (2013.01); *A23V 2002/00* (2013.01); *B01D 2311/04* (2013.01); *B01D 2311/06* (2013.01); *B01D 2311/2626* (2013.01); *B01D 2311/2676* (2013.01); *B01D 2315/16* (2013.01); *B01D 2325/20* (2013.01)

(58) Field of Classification Search

CPC ....... C07H 1/06; C08B 37/0003; A23L 33/40; A23L 1/308

USPC ........................................................ 536/127

See application file for complete search history.

(56) References Cited

U.S. PATENT DOCUMENTS

| | | | | |
|---|---|---|---|---|
| 5,057,326 | A | 10/1991 | Sampson | |
| 7,521,212 | B1 | 4/2009 | Samain et al. | |
| 10,377,787 | B2 * | 8/2019 | Jennewein | A23L 33/21 |
| 10,435,427 | B2 | 10/2019 | Jennewein et al. | |
| 10,882,880 | B2 * | 1/2021 | Jennewein | A23L 29/30 |
| 11,168,105 | B2 * | 11/2021 | Jennewein | A61P 1/00 |
| 11,597,740 | B2 * | 3/2023 | Jennewein | A61P 1/04 |
| 11,834,691 | B2 * | 12/2023 | Jennewein | C07H 3/08 |
| 11,912,735 | B2 * | 2/2024 | Jennewein | A23L 33/125 |
| 2004/0167220 | A1 | 8/2004 | Horst et al. | |
| 2007/0002073 | A1 | 1/2007 | Baik et al. | |
| 2007/0020736 | A1 | 1/2007 | Samain | |
| 2016/0237104 | A1 | 8/2016 | Jennewein et al. | |
| 2020/0231618 | A1 | 7/2020 | Jennewein | |
| 2020/0308211 | A1 | 10/2020 | Jennewein et al. | |
| 2021/0061836 | A1 | 3/2021 | Jennewein | |

FOREIGN PATENT DOCUMENTS

| | | | | |
|---|---|---|---|---|
| KR | 20160132009 | A | 11/2016 | |
| WO | 2009135252 | A1 | 11/2009 | |
| WO | 2010106320 | A2 | 9/2010 | |
| WO | 2010115935 | A1 | 10/2010 | |
| WO | 2015049331 | A1 | 4/2015 | |
| WO | WO 2015/106943 | A1 * | 7/2015 | A23L 33/40 |
| WO | 2016095924 | A1 | 6/2016 | |
| WO | 2017182965 | A1 | 10/2017 | |
| WO | 2018020473 | A1 | 2/2018 | |

(Continued)

OTHER PUBLICATIONS

Geisser et al, Journal of Chromatography A, 2005, 1092, 17-23.*

Stefan Weichert, et al., "Structural basis for norovirus inhibition by human milk oligosaccharides,." Journal of Virology, (2016), vol. 90, No. 9: 4843-4848.

L. Bode, "Human milk oligosaccharides: Every baby needs a sugar mama," Glycobiology, (2012), vol. 22, No. 9 :1147-1162.

L. Bode and E. Jantscher-Krenn, "Structure-Function Relationships of Human Milk Oligosaccharides," Advances in Nutrition, (2012), vol. 3, No. 3: 383S-391S.

Florian Baumgartner, et al., "Construction of *Escherichia coli* strains with chromosomally integrated expression cassettes for the synthesis of 2'-fucosyllactose," Microbial cell factories, (2013), vol. 12, No. 1 : 1-13.

(Continued)

*Primary Examiner* — Ganapathy Krishnan

(74) *Attorney, Agent, or Firm* — Kelly K. Reynolds

(57) ABSTRACT

Disclosed is method for the purification of an oligosaccharide of interest from a fermentation broth, the method comprises providing a cell-free fermentation broth to a first filtration step using a nanofiltration membrane, thereby providing a filtrate which contains the oligosaccharide of interest; subjecting the filtrate to a second filtration step using a nanofiltration membrane, thereby providing a retentate which contains the oligosaccharide of interest; and removing salts from the retentate thereby providing a purified preparation of the oligosaccharide of interest.

20 Claims, 6 Drawing Sheets

(56) References Cited

FOREIGN PATENT DOCUMENTS

| WO | 2019043029 A1 | 3/2019 |
|---|---|---|
| WO | 2019215073 A1 | 11/2019 |

OTHER PUBLICATIONS

Bernard Priem, et al., "A new fermentation process allows large-scale production of human milk oligosaccharides by metabolically engineered bacteria," Glycobiology, (2002), vol. 12, No. 4 : 235-240.
Stefan Weichert, et al., "Bioengineered 2'-fucosyllactose and 3-fucosyllactose inhibit the adhesion of Pseudomonas aeruginosa and enteric pathogens to human intestinal and respiratory cell lines," Nutrition research, (2013), vol. 33, No. 10:831-838.
Trisha Gura, "Nature's first functional food," Science, (2014), vol. 345, No. 6198: 747-749.
Ardythe L. Morrow, et al., "Human milk oligosaccharides are associated with protection against diarrhea in breast-fed infants," The Journal of Pediatrics, (2004), vol. 145, No. 3: 297-303.
International Search Report for Application No. PCT/EP2020/061888 mailed Aug. 5, 2020.
Christoph Albermann, et al., "Synthesis of the milk oligosaccharide 2'-fucosyllactose using recombinant bacterial enzymes," Carbohydrate Research, (2001), vol. 334, 97-103.
Florian Baumgartner, et al., "Synthesis of the Human Milk Oligosaccharide Lacto-NTetraose in Metabolically Engineered, Plasmid-Free *E. coli*," Chem Bio Chem Communications, (2014), vol. 1896-1900.
Nicolas Fierfort and Eric Samain, "Genetic engineering of *Escherichia coli* for the economical production of sialylated oligosaccharides," Journal of Biotechnology, (2008), vol. 134, 261-265.
Caroline Gebus, et al., "Synthesis of a-galactosyl epitopes by metabolically engineered *Escherichia coli*," Carbohydrate Research, (2012), vol. 361, 83-90.
Sang Yup Lee, et al., "Systems metabolic engineering, industrial biotechnology and microbial cell factories," Microbial Cell Factories, (2012), vol. 11, No. 156, 1-3.
Clemens Kunz and Heinz Egge, "Chapter 1: From Bifidus Factor to Human Milk Oligosaccharides: A Historical Perspective on Complex Sugars in Milk," Prebiotics and Probiotics in Human Milk Origins and Functions, (2016), 3-16.
Tatsuo Miyazaki, et al., "Chapter 24: Enzymatic Synthesis of Lacto-N-Difucohexaose I Which Binds to *Helicobacter pylori*," Methods in Enzymology, (2010), vol. 480, 511-524.
Takeomi Murata, et, al, "Facile enzymatic conversion of lactose into lacto-N-tetraose and lacto-N-neotetraose," Glycoconjugate Journal, (1999), vol. 16, 189-195.
Rune T. Nordvang, et al., "Separation of 30-sialyllactose and lactose by nanofiltration: A trade-off between charge repulsion and pore swelling induced by high pH," Separation and Purification Technology, (2014), vol. 138, 77-83.
Altmann et al., 2016, Food Bioprocess Technol 9: 1924-1936.
Córdova et al., 2017, Chemical Engineering Research and Design, 117, 488-499.
Montesdeoca et al., 2016, Journal of Membrane Science, 520, 712-722.

* cited by examiner

PURIFICATION OF OLIGOSACCHARIDES FROM A FERMENTATION BROTH BY USING FILTRATION

CROSS-REFERENCE TO RELATED APPLICATIONS

This application is the National Stage entry of International Application No. PCT/EP2020/061888, filed 29 Apr. 2020, which claims priority to European Patent Application No. 19175716.0, filed 21 May 2019.

BACKGROUND

Field

The present invention relates to the production of oligosaccharides by microbial fermentation in an industrial scale. More specifically, the present invention relates to the purification of an oligosaccharide of interest from a fermentation broth by using filtration methods.

Description of Related Art

Human milk is a complex mixture of carbohydrates, fats, proteins, vitamins, minerals and trace elements. The carbohydrate fraction is the most abundant solids fraction, and can be divided further into lactose and more complex oligosaccharides, the so-called human milk oligosaccharides (HMOs).

Whereas lactose is used as an energy source, the complex oligosaccharides are not metabolized by infants or adults. The fraction of complex oligosaccharides accounts for up to 10% of the total carbohydrate fraction and probably consists of more than 150 different oligosaccharides. The occurrence and concentration of these complex oligosaccharides are specific to humans and therefore they are not found in large quantities in the milk of other mammals, such as domesticated dairy animals. Although HMOs represent only a minor fraction of total human milk, their highly beneficial effect on the development of breastfed infants has become evident over the past decades.

The most prominent HMO is 2'-fucosyllactose. Further prominent HMOs are 3-fucosyllactose, difucosyllactose, lacto-N-tetraose, lacto-N-neotetraose and lacto-N-fucopentaoses. As well as these neutral oligosaccharides, acidic HMOs can also be found in human milk, including 3'-sialyllactose, 6'-sialyllactose and sialyllacto-N-tetraoses such as LST-a, LST-b and LST-c (Table 1). Up to 20% of the total HMO content of human milk is acidic due to the presence of at least one sialic acid moiety. These structures are closely related to the epitopes of epithelial cell surface glycoconjugates (Lewis histoblood group antigens) and the structural homology between HMOs and epithelial epitopes explains the ability of HMOs to protect against bacterial pathogens (Weichert et al. 2013, *Nutr. Res.* 33:831; Weichert et al. 2016, *J. Virol.* 90:4843).

The presence of complex oligosaccharides in human milk has been known for a long time and the physiological functions of HMOs have been the subject of medical research for many decades (Gura 2014, *Science* 345:747; Kunz & Egge 2017, In McGuire, McGuire & Bode (eds) Prebiotics and Probiotics in Human Milk, Elsevier, London, pp. 3-16). For some of the more abundant HMOs, specific functions have already been identified (Bode 2012, *Glycobiology* 22:147; Bode & Jantscher-Krenn 2012, *Adv. Nutr.* 3S:383; Morrow et al. 2004, *J. Pediatr.* 145:297). Due to their physiological ability to inhibit infectious agents (bacteria, viruses and bacterial toxins), their positive effects on brain development and their prebiotic functions, there is a great demand to include HMOs in food products, particularly infant nutrition products. Table 1 provides an overview of the HMOs that can be purified from a fermentation broth by the methods disclosed herein.

TABLE 1

A list of human milk oligosaccharides that can be purified by a method disclosed herein.

| Name | Abbrev. | structure |
|---|---|---|
| 2'-Fucosyllactose | 2'-FL | Fuc(α1-2)Gal(β1-4)Glu |
| 3-Fucosyllactose | 3-FL | Gal(β1-4)Glu<br>\|<br>Fuc(α1-3) |
| 2',3-Difucosyllactose | DF-L | Fuc(α1-2)Gal(β1-4)Glu<br>\|<br>Fuc(α1-3) |
| Lacto-N-triose II | LNT II | GlcNAc(β1-3)Gal(β1-4)Glu |
| Lacto-N-tetraose | LNT | Gal(β1-3)GlcNAc(β1-3)Gal(β1-4)Glu |
| Lacto-N-neotetraose | LNnT | Gal(β1-4)GlcNAc(β1-3)Gal(β1-4)Glu |
| Lacto-N-fucopentaose I | LNFP I | Fuc(α1-2)Gal(β1-3)GlcNAc(β1-3)Gal(β1-4)Glu |
| Lacto-N-neofucopentaose I | LNnFP I | Fuc(α1-2)Gal(β1-4)GlcNAc(β1-3)Gal(β1-4)Glu |
| Lacto-N-fucopentaose II | LNFP II | Gal(β1-3)GlcNAc(β1-3)Gal(β1-4)Glu<br>\|<br>Fuc(α1-4) |
| Lacto-N-fucopentaose III | LNFP III | Gal(β1-4)GlcNAc(β1-3)Gal(β1-4)Glu<br>\|<br>Fuc(α1-3) |

TABLE 1-continued

A list of human milk oligosaccharides that can be purified by a method disclosed herein.

| Name | Abbrev. | structure |
|---|---|---|
| Lacto-N-fucopentaose V | LNFP V | Gal(β1-3)GlcNAc(β1-3)Gal(β1-4)Glu<br>Fuc(α1-3) |
| Lacto-N-neofucopentaose V | LNnFP V | Gal(β1-4)GlcNAc(β1-3)Gal(β1-4)Glu<br>Fuc(α1-3) |
| Lacto-N-difucohexaose I | LNDH I | Gal(β1-3)GlcNAc(β1-3)Gal(β1-4)Glu<br>Fuc(α1-2) Fuc(α1-4) |
| Lacto-N-difucohexaose II | LND | Gal(β1-3)GlcNAc(β1-3)Gal(β1-4)Glu<br>Fuc(α1-4) Fuc(α1-3) |
| 6'-Galactosyllactose | 6'-GL | Gal(β1-6)Gal(β1-4)Glu |
| 3'-Galactosyllactose | 3'-GL | Gal(β1-3)Gal(β1-4)Glu |
| Lacto-N-hexaose | LNH | Gal(β1-4)GlcNAc(β1-6)Gal(β1-4)Glu<br>Gal(β1-3)GlcNAc(β1-3) |
| Lacto-N-neohexaose | LNnH | Gal(β1-4)GlcNAc(β1-6)Gal(β1-4)Glu<br>Gal(β1-4)GlcNAc(β1-3) |
| para-Lacto-N-hexaose | paraLNT | Gal(β1-3)GlcNAc(β1-3)Gal(β1-4)GlcNAc(β1-3)Gal(β1-4)Glu |
| para-Lacto-N-neohexaose | paraLNnH | Gal(β1-4)GlcNAc(β1-3)Gal(β1-4)GlcNAc(β1-3)Gal(β1-4)Glu |
| Difucosyl-lacto-N-neohexaose | DF-LNnH | Fuc(α1-3)<br>Gal(β1-4)GlcNAc(β1-6)Gal(β1-4)Glu<br>Gal(β1-4)GlcNAc(β1-3)<br>Fuc(α1-3) |
| 3'-Sialyllactose | 3'-SL | Neu5Ac(α2-3)Gal(β1-4)Glu |
| 6'-Sialyllactose | 6'-SL | Neu5Ac(α2-6)Gal(β1-4)Glu |
| Lacto-N-sialylpentaose a | LST-a | Neu5Ac(α2-3)Gal(β1-3)GlcNAc(β1-3)Gal(β1-4)Glu |
| Lacto-N-sialylpentaose b | LST-b | Gal(β1-3)GlcNAc(β1-3)Gal(β1-4)Glu<br>Neu5Ac(α2-6) |
| Lacto-N-sialylpentaose c | LST-c | Neu5Ac(α2-6)Gal(β1-4)GlcNAc(β1-3)Gal(β1-4)Glu |
| Fucosyl-lacto-N-sialylpentaose a | F-LST-a | Neu5Ac(α2-3)Gal(β1-3)GlcNAc(β1-3)Gal(β1-4)Glu<br>Fuc(α1-4) |
| Fucosyl-lacto-N-sialylpentaose b | F-LST-b | Fuc(α1-2)Gal(β1-3)GlcNAc(β1-3)Gal(β1-4)Glu<br>Neu5Ac(α2-6) |
| Fucosyl-lacto-N-sialylpentaose c | F-LST-c | Neu5Ac(α2-3)Gal(β1-3)GlcNAc(β1-3)Gal(β1-4)Glu<br>Fuc(α1-3) |
| Disialyl-lacto-N-tetraose | DS-LNT | Neu5Ac(α2-3)Gal(β1-4)GlcNAc(β1-3)Gal(β1-4)Glu<br>Neu5Ac(α2-6) |
| Disialyl-lacto-N-fucopentaose | DS-LNFP | Neu5Ac(α2-3)Gal(β1-4)GlcNAc(β1-3)Gal(β1-4)Glu<br>Neu5Ac(α2-6) Fuc(α1-3) |

TABLE 1-continued

A list of human milk oligosaccharides that can be purified by a method disclosed herein.

| Name | Abbrev. | structure |
|---|---|---|
| 3-Fucosyl-3'-sialyllactose | 3F-3'-SL | Neu5Ac(α2-3)Gal(β1-4)Glu<br>Fuc(α1-3) (on Glu) |
| 3-Fucosyl-6'-sialyllactose | 3F-6'-SL | Neu5Ac(α2-6)Gal(β1-4)Glu<br>Fuc(α1-3) (on Glu) |
| Lacto-N-neodifucohexaose | LNnDFH I | Gal(β1-4)GalNAc(β1-3)Gal(β1-4)Glu<br>Fuc(α1-3) (on GalNAc) Fuc(α1-3) (on Glu) |

The limited supply of individual HMOs and the inability to source sufficient quantities of these molecules has led to the development of processes based on chemical synthesis to generate them. However, the chemical synthesis of HMOs has proven extremely challenging, especially large-scale production of HMOs with sufficient quality for food applications. In particular, the chemical synthesis of HMOs such as 2'-FL (WO 2010/115935 A) requires several noxious chemicals, which may contaminate the final product.

The drawbacks of chemical synthesis have led to the development of several enzymatic and fermentation-based methods (Miyazaki et al. 2010, *Methods Enzymol.* 480:511; Murata et al. 1999, *Glycoconj. J.* 16:189; Baumgartner et al. 2013, *Microb. Cell Fact.* 12:40; Lee et al. 2012, *Microb. Cell Fact.* 1:48; Albermann et al. 2001, *Carbohydr. Res.* 334:97; U.S. Pat. No. 7,521,212 B1; Fierfort & Samain 2008, *J. Biotechnol.* 134:216). However, these processes yield complex mixtures of oligosaccharides, and the desired product is therefore contaminated with starting materials such as lactose, as well as intermediates, unwanted by-products (e.g. by-products originating from side activities of certain glycosyltransferases) and substrates from the fermentation process such proteins, polypeptides, organic acids, and salts.

Many current methods for the purification of individual oligosaccharides from mixtures are technically complex, difficult to scale up, and uneconomical for food applications. Industrial-scale processes have been developed to purify the disaccharides lactose and sucrose from whey and molasses, respectively, but these methods involve multiple crystallization steps which are elaborate and achieve only low yields. However, whey and molasses are “food grade” products to start with and nowhere near as complex and demanding (in terms of regulatory requirements) as fermentation broths containing recombinant bacteria or yeast. Gel filtration chromatography is the best method for the purification of complex oligosaccharides such as HMOs produced by microbial fermentation, but the disadvantages of this method include its lack of scalability and its incompatibility with continuous processing. Gel filtration chromatography is therefore uneconomical and cannot be used to produce HMOs on an industrial scale.

Theoretically, gel-filtration chromatography is the best method for the purification of complex oligosaccharides such as HMOs produced by microbial fermentation, but the disadvantages of gel-filtration chromatography include its lack of scalability and its incompatibility with continuous processing. Gel-filtration chromatography is therefore uneconomical and can not be used to produce HMOs in an industrial scale.

Following the development of efficient methods and processes for the production of HMOs by microbial fermentation, the next logical step was the development of efficient downstream processes to isolate the HMOs from the culture broth.

WO2015/049331 A discloses a process for the purification of a neutral HMO. The process uses ion exchange, electrodialysis and simulated moving bed (SMB) chromatography to achieve the continuous and efficient purification of large quantities of HMOs. Unlike chemical synthesis routes for the production of neutral HMOs and their subsequent purification, the described fermentation and purification process allows the provision of HMOs free of noxious chemicals, such as trace heavy metals and organic solvents. The purification method yields a highly purified HMO product in solid form (by spray drying) or as a concentrated syrup, which can used in food applications.

WO 2015/106943 A describes a simple process for the purification of neutral HMOs produced by microbial fermentation. The process uses a combination of cation exchange, anion exchange and nanofiltration and/or electrodialysis, which allows the efficient purification of large quantities of neutral HMOs. Unlike earlier purification methods for neutral HMOs produced by microbial fermentation, the process does not involve chromatographic separation steps. The process yields HMOs in solid form as spray dried material, as crystalline material, or as a filter-sterilized concentrate. The resulting HMOs are free of proteins and materials originating from the recombinant microbial strains used for production, and are thus ideal for food, medical food and feed (e.g. pet food) applications.

WO 2016/095924 A describes a method to purify 2'-FL by crystallization. The HMO was produced by microbial fermentation, and following the removal of biomass it was concentrated by nanofiltration and electrodialysis. Finally, the 2'-FL was selectively crystallized from an aqueous solution also containing 2', 3-di-O-fucosyllactose (DFL) using acetic acid.

LNT and LNnT can be separated from carbohydrate by-products by selective binding to active charcoal, followed by elution with organic solvents and separation by gel filtration chromatography (Priem et al. 2002, *Glycobiology* 12:235; Gebus et al. 2012, *Carbohydr. Res.* 361:83; Baumgartner et al. 2014, *ChemBioChem* 15:1896). As stated above, gel filtration chromatography is a convenient laboratory-scale method but it cannot be efficiently scaled up for industrial production.

WO 2015/049331 A disclosed the following sequence of operations to purify LNT produced by bacterial fermentation to provide a clear, particle-free solution: electrodialysis, nanofiltration, simulated-moving bed chromatography (SMB) using a strong cation exchange resign, electrodialysis, ultrafiltration and a second SMB chromatography step.

Various methods have also been described for the isolation of acidic HMOs, especially sialylated lactoses or sialylated oligosaccharides.

US 2007/0020736 A disclosed the production of 3'-SL with disialylated and trisialylated lactoses as by-products of a genetically modified strain of the bacterium *Escherichia coli*. The 3'-SL accumulated in the culture broth to a concentration of ~0.8 mM. The 3'-SL was purified using the following steps: centrifugation, adsorption by passing the supernatant over charcoal and washing out the water-soluble salts with distilled water, gradient elution in aqueous ethanol and finally separation on a Biogel column and desalting. The yield from 1 L of broth was 49 mg 3'-SL.

Another disclosed method involves the production of 3'-SL using a genetically modified *E. coli* strain and subsequent isolation by heat permeabilization of the cells followed by centrifugation (Priem et al. 2002, *Glycobiology* 12:235). The material in the supernatant was adsorbed onto charcoal and the water-soluble salts were washed out with distilled water. After gradient elution in aqueous ethanol, the 3'-SL was adsorbed to a strong anion exchanger in its $HCO_3^-$ (bicarbonate ion) form and eluted with a linear gradient of sodium bicarbonate ($NaHCO_3$). The latter was removed by cation exchange (using the resin in its acidic form), resulting in a 3'-SL recovery efficiency of 49%.

An alternative procedure starting with fermentation broth comprised the steps of heat permeabilization, centrifugation, pH adjustment to 3.0 by adding a strong cation exchange resin in its acid form, and the removal of precipitated proteins by centrifugation (Fierfort et al. 2008, *J. Biotechnol.* 134:261). The pH of the supernatant was then adjusted to 6.0 by adding a weak anion exchanger in its basic form and the 3'-SL was bound to an anion exchanger in $HCO_3^-$ form. After washing with distilled water followed by elution in a continuous $NaHCO_3$ gradient, the $NaHCO_3$ was removed by cation exchange (using the resin in its acidic form) until the pH fell to 3.0. Finally, the pH was adjusted to 6.0 with NaOH. This purification strategy achieved a 3'-SL recovery efficiency of 59%.

Enzymatically produced 3'-SL has also been separated from lactose by nanofiltration (Nordvang et al. 2014, *Separ. Purif. Technol.* 138:77). The authors showed that two different nanofiltration membranes, one with a molecular weight cut-off (MWCO) of 600-800 Da (sulfonated polyethersulfone (SPES) membrane) and the other with a MWCO of 1000-1400 Da (SPES membrane), could separate most of the 3'-SL from the lactose after diafiltration. However, there was significant loss of 3'-SL during this process and the purity was low, requiring an additional ion exchange purification step.

WO 2010/106320 A2 describes a method to enrich 3'-SL from whey. First, the proteins are removed by ultrafiltration, and then the clarified whey permeate is incubated with an ion exchange resin to capture the 3'-SL. Following elution from the ion exchange material, the enriched 3'-SL fraction is concentrated by nanofiltration to demineralize the concentrate. After demineralization the 3'-SL is concentrated and dried, yielding a final dry product with a 3'-SL content of 20%-wt.

WO 2018/020473 A describes an additional process for the enrichment of 3'-SL and 6'-SL from a liquid source. Both HMOs were isolated from the mother liquor of a lactose crystallization by heating the solution, enzyme treatment and additional ultrafiltration and nanofiltration steps. After enrichment the content of 3'-SL and 6'-SL was 10-30%-wt. of the dry mass.

Starting from this prior art, it was an objective to provide a process for the purification of oligosaccharides of interest, in particular neutral HMOs or sialylated HMOs, that have been produced by microbial fermentation, wherein said process is easy to scale up and suitable for commercial or industrial scale manufacturing of said oligosaccharides of interest, and which may lead to a product having a purity which renders the product suitable for human consumption.

It must be stressed that microbial fermentation broth, particularly that containing recombinant microorganisms (bacteria or eukaryotic microorganisms such as backer's yeast) is much more complex than dairy-derived product streams. The composition of whey for example is ~94% water, 4-5% lactose, 0.5-1% of proteins and only few defined minerals like calcium, potassium and phosphor beside some vitamins, simple matrix which is just concentrated and demineralized in dairy streams. In contrast the matrix of the sugar solution obtained from recombinant microbial fermentation process is highly complex, starting first with the requirement by law to separate recombinant biomass and inactivation thereof according governmental regulations. The obtained clarified broth is an undefined matrix of different salts and ions, also containing heavy metals and trace elements. Challenge of such a liquid is in addition the removal of cell debris, membrane fragments like lipids, proteins, molecules originated from microbial cell metabolism and especially DNA. Recovery of an oligosaccharide, produced via recombinant processing aid like genetically modified bacteria, is therefore even more a challenge in comparison to whey and dairy streams, because variety of contaminants inside the broth is very high with respect to molecular weight, charged molecules (single charged and multiple charged) and colourizing molecules.

SUMMARY

The present invention provides a method for the purification of an oligosaccharide of interest produced by fermentation in a batch manner or in a continuous manner from a culture broth or fermentation broth obtained by microbial fermentation using recombinant fermentation strains. Previously described purification strategies often employed expensive ion exchange steps (requiring both cation and anion exchangers). Ion exchangers cannot be operated continuously because they require regeneration. The culture broth contains the oligosaccharide of interest, biomass, medium components, salts, and contaminants such as other acids and pigments.

During the purification process, the culture broth can undergo the following purification steps to obtain the target oligosaccharide:

1) Separation of microbial cells from the culture broth by microfiltration
2) Separation of proteins from the clarified culture broth (=process stream) by ultrafiltration
3) First nanofiltration step to remove peptides and high-molecular-weight (HMW) impurities
4) Second nanofiltration step to remove water and salts
5) Activated charcoal treatment to remove pigments and other impurities
6) Electrodialysis or diafiltration using a nanofiltration membrane for complete removal of contaminating salts
7) Removal of water by reverse osmosis Additionally, another electrodialysis step could be introduced before activated charcoal treatment to reduce the quantity of contaminating ions. To prepare the oligosaccharide of interest in solid form after purification in aqueous solution, the material could be either spray-dried or granulated.

DETAILED DESCRIPTION

Figure 1:
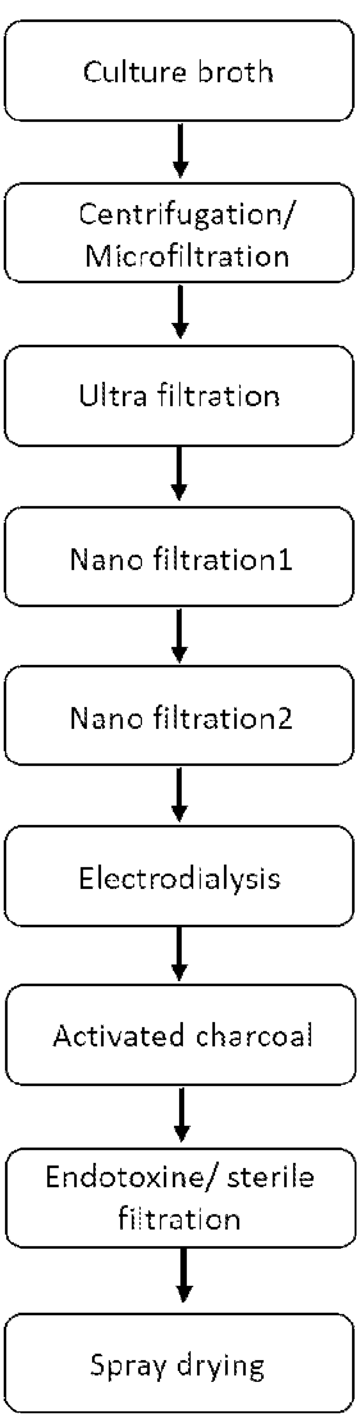
FIG. 1 shows a process scheme of an exemplary embodiment of the method according to the invention.
Figure 2:
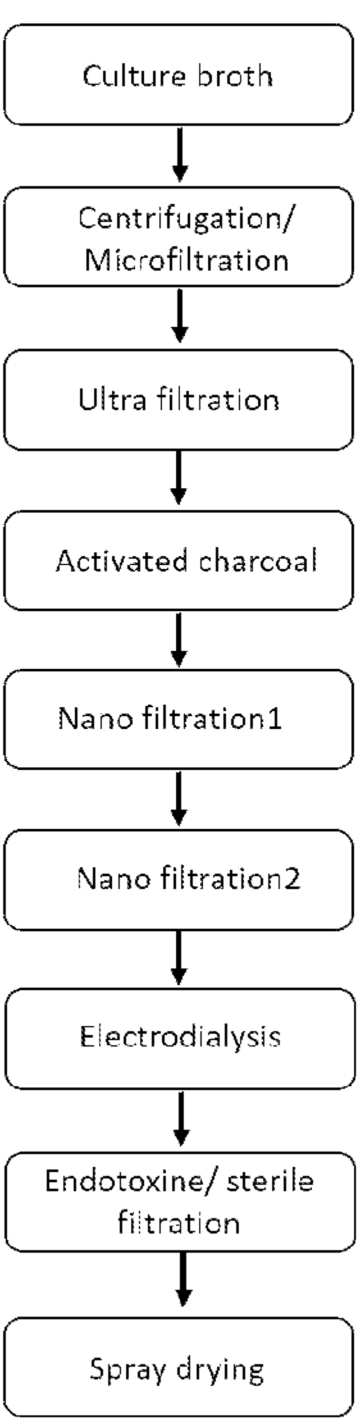
FIG. 2 shows a process scheme of another exemplary embodiment of the method according to the invention.
Figure 3:
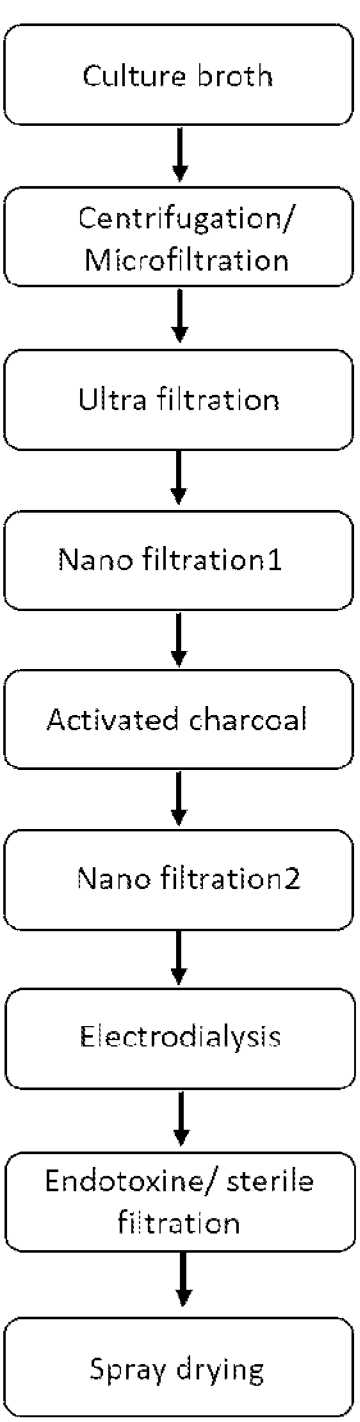
FIG. 3 shows a process scheme of another exemplary embodiment of the method according to the invention.
Figure 4:
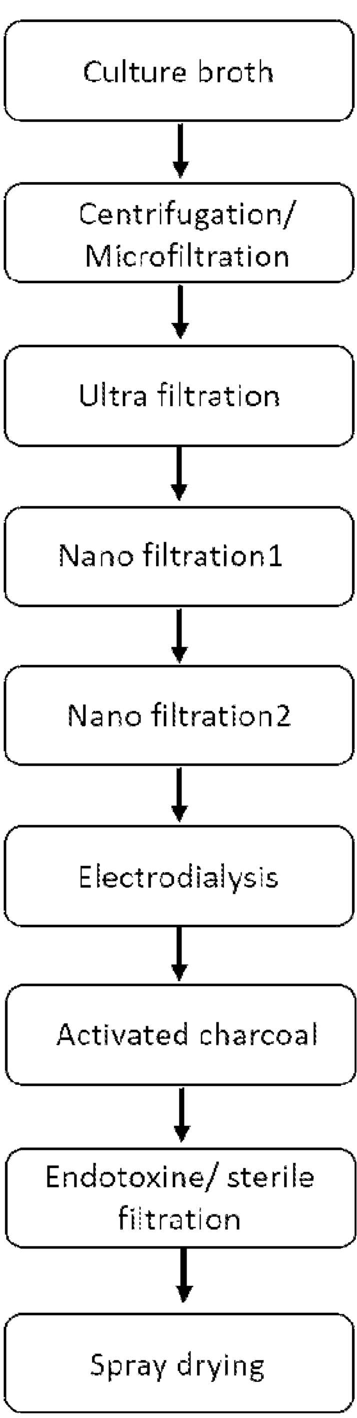
FIG. 4 shows a process scheme of another exemplary embodiment of the method according to the invention.
Figure 5:
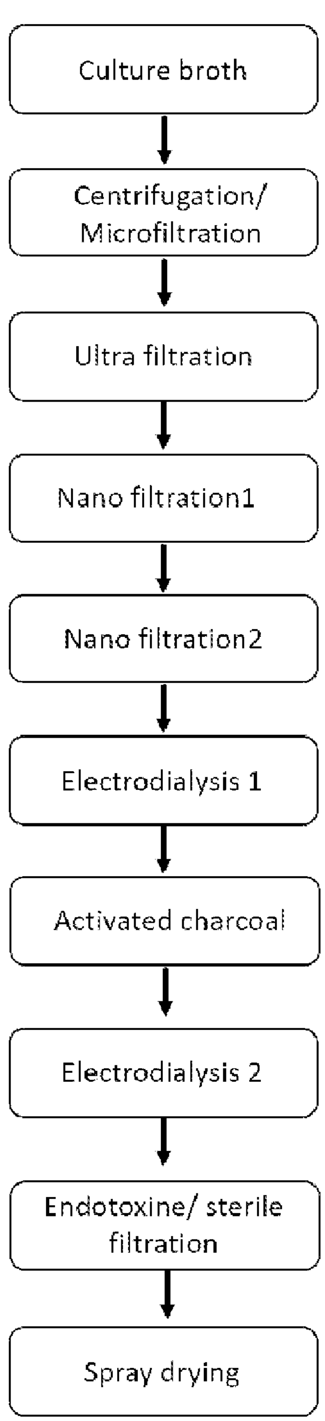
FIG. 5 shows a process scheme of another exemplary embodiment of the method according to the invention.

According to the invention, the term "purity" refers to chemical purity and specifies the degree to which a substance, such as 2'-FL, 3-FL, DFL, LNT, 3'-SL, 6'-SL or any other oligosaccharide of interest (Table 1), is undiluted or unmixed with extraneous material. Hence, the chemical purity is an indicator of the relationship between a single substance and any by-products/impurities. Chemical purity is expressed as a percentage (%) and is calculated using the following formula:

$$\text{Percent Purity} = \frac{\text{Mass of desired product}}{\text{Total mass of sample}} \times 100$$

In a composition comprising an oligosaccharide of interest, the purity of this compound can be determined by any suitable method known to the skilled artisan, such as high-performance liquid chromatography (HPLC). An appropriate detector can be selected from the group consisting of an electrochemical detector, a refractive-index (RI) detector, a mass spectrometer (MS), a diode-array detector (DAD), and a nuclear magnetic resonance (NMR) detector. In HPLC for example, purity can be determined by calculating the ratio of the area underneath the target peak (representing the amount of the oligosaccharide of interest) to the sum of areas underneath all peaks (representing both the amount of the oligosaccharide of interest and compounds different to this substance in the same chromatogram). However, this implies that all impurities can be analysed by the chosen HPLC method. Otherwise, a mass-balance approach is necessary, i.e. an absolute quantification of the desired product. In said approach, pure substances are used as a reference to quantify the purity, which is then judged against the dry matter obtained from the product (desired product plus all impurities). Said mass-balance approach can also be used to determine purity according to the invention.

According to the invention, a "culture broth" or "fermentation broth" refers to any liquid after fermentation containing 2'-FL, 3-FL, DFL, LNT, 3'-SL, 6'-SL or any other oligosaccharide of interest (Table 1) to be purified. The terms "culture broth", "fermentation broth" and "culture medium" are used as synonyms herein. The culture broth comprises an oligosaccharide of interest which is to be purified as well as biomass (e.g. biological cells and cell debris), medium components, salts and further contaminants such as other acids and pigments. The biological cells contained in the culture broth are biological cells that produce the oligosaccharide of interest intracellularly and secretes this compound into the liquid culture medium. The biological cells can comprise or consist of genetically modified biological cells, for example genetically modified *E. coli* cells. The genetic modification can comprise or consist of a modification to produce an oligosaccharide of interest, especially during the growth phase of said biological cells.

The term "biomass" as used herein refers to the entirety of biological cells present in the fermentation broth at the end of the fermentation step. The biomass includes the microbial cells that produced the oligosaccharide of interest, cells descended from this microorganism that may have lost their ability to produce the oligosaccharide of interest during the fermentation step, as well as any other cells that are unintentionally present in the fermentation broth at the end of the fermentation step. Hence, essentially all biological cells that are present in the fermentation broth at the end of the fermentation step are separated from the fermentation broth such that the clarified fermentation broth, known as the "process stream" (any solution comprising or containing the oligosaccharide of interest which are to be purified) is substantially or entirely free of cells.

The biomass preferably comprises biological cells that produce an oligosaccharide of interest, preferably bacterial cells that produce the oligosaccharide of interest, and more preferably recombinant bacterial cells that produce the oligosaccharide of interest, most preferably recombinant *E. coli* cells that produce the oligosaccharide of interest.

The biomass and/or the microbial cells can be removed from the fermentation broth by centrifugation and/or filtration.

In centrifugation methods suitable for the removal of biomass from the culture broth, the biomass is obtained as a pellet and the supernatant as a clarified process stream which is subjected to further treatments. In suitable filtration methods for the removal of biomass from the culture broth, the filtrate becomes the clarified process stream. The preferred filtration method for biomass removal is microfiltration and/or ultrafiltration, the latter conferring the ability to remove even smaller particles than microfiltration and also large molecules. Microfiltration and ultrafiltration can be operated in dead-end filtration mode (process stream flows perpendicular to the filter) or cross-flow filtration mode (process stream flows parallel to the filter).

Microfiltration is a physical separation process wherein a particle-containing fluid is passed through a medium, said medium comprising either a porous substance containing torturous channels to retain particles (depth filtration) and/or a membrane with a specific pore size allowing the passage of particles/molecules that are smaller than said pore size (membrane filtration). The term "microfiltration" as used herein refers to a physical separation process wherein biological cells (and cell debris) are removed from the fermentation broth leaving a (clarified) process stream.

Suitable membranes for the removal of biomass by microfiltration may have a pore size of at least 0.2 μm and could be a hollow-fibre or spiral-wound membranes. Alternatively, the removal of biomass could be achieved by microfiltration using membranes with a MWCO of 100-1000 kDa, preferably 150-500 kDa, to remove the biomass, additional cell debris and larger proteins. For example, membranes such as the TRISEP® DS MVP20 (pore size 0.2 μm) (Microdyn-Nadir GmbH, Wiesbaden, Germany) which is spirally wound to provide a compact design and better performance, can be used to separate the cells from the culture broth. Also spiral-wound membranes with a pore size of 0.05-0.1 μm like the TRISEP® DS MP005, which is a module comprising a PES membrane and a nominal pore size of 0.05 μm, can be used for separation of the biomass and proteins.

Additionally, hollow-fibre modules like the FS10-FC FUS1582 (Microdyn-Nadir GmbH), a hollow-fibre filtration module using a PES membrane (5 $m^2$) with a MWCO of 150 kDa, can be used as alternative.

In summary, the following possibilities for the removal of biomass from the fermentation broth can be applied in the present invention:

i) Harvest by centrifugation. Insoluble components are removed from the culture broth in one step. Advantage: rapid removal of insoluble components.

ii) Harvest by microfiltration. Insoluble components and large molecules above a certain size are removed from the culture broth in one step. Spiral-wound membranes or hollow-fibre cross-flow filters can be used for microfiltration with a MWCO 500 kDa, Advantage: rapid removal of insoluble components and large soluble molecules above a certain size.

iii) Harvest by centrifugation combined with microfiltration: Insoluble components and large molecules above a certain size are removed from the culture broth in two steps. Spiral-wound membranes or hollow-fibre cross-flow filters can be used for microfiltration with a MWCO 500 kDa, Advantage: rapid removal of insoluble components and large molecules above a certain size without clogging the microfiltration membranes.

Ultrafiltration is a form of membrane filtration that is not fundamentally different to microfiltration. In ultrafiltration, forces generated by pressure and concentration gradients lead to the removal of particles and large soluble molecules by passing the liquid containing such particles and large soluble molecules through a semipermeable membrane. This causes the particles and large soluble molecules to be retained in the so-called retentate, while water and low-molecular-weight (LMW) solutes such as the produced neutral and acidic oligosaccharides pass through the membrane into the permeate (filtrate). Membranes for ultrafiltration are defined by their MWCO, which describes the maximum molecular weight of a soluble molecule that can pass through the membrane in to the permeate. Any particles, as well as molecules larger than the MWCO, are unable to pass through the membrane and remain in the retentate. Ultrafiltration may be applied in cross-flow mode, where the flow of the liquid is parallel to the membrane surface, or in dead-end mode, where the flow of the liquid is perpendicular to the membrane surface.

The clarified process stream comprising the produced oligosaccharide of interest usually contains a substantial quantity of undesired impurities including (but not limited to) monovalent ions, divalent ions, amino acids, polypeptides, proteins, organic acids, nucleic acids, monosaccharides and/or oligosaccharides.

Suitable membranes for the removal of most proteins by ultrafiltration have a MWCO of at least 50 kDa, preferably at least 30 kDa, more preferably 10 kDa and could be a hollow-fibre or spiral-wound membranes. For example, membranes such as SPIRA-CEL® DS UP010 (MWCO=10 kDa) or SPIRA-CEL DS UP005 (MWCO=5 kDa), both of which are marketed by Microdyn-Nadir GmbH, are spirally wound to provide a compact design and better performance, and these can be used to separate the remaining protein from the cell-free culture broth.

Additionally, hollow-fibre modules such as the ROMICON® HF UF Cartridge PM10 (Koch Membranes Systems, Wilmington, USA), which are PES membranes with an area of up to 12 $m^2$ and a MWCO of 10 kDa, can be used as alternative.

Nanofiltration is a membrane filtration method in which the membrane contains nanometre-sized pores (1-10 nm). The pore size of nanofiltration membranes is smaller than that of microfiltration and ultrafiltration membranes, but larger than that of membranes used for reverse osmosis. Nanofiltration membranes are predominantly made from thin films of polymers such as polyethylene terephthalate or metals such as aluminium, with pore densities of $1\text{-}10^6$ pores per $cm^2$.

Nanofiltration is used in the purification method for oligosaccharide of interest to remove LMW impurities such as peptides and salts, and to increase the concentration of the oligosaccharides in the clarified process stream or eluate.

The molecular weight of most HMOs ranges from 400 to 1,200 Da. To remove HMW impurities (>1200 Da) such as peptides and pigments as well as LMW impurities (<400 Da) such as salts from the process stream, at least two nanofiltration steps are required.

After ultrafiltration, all molecules >5 kDa or >10 kDa (depending on the membrane used) should have been removed from the process stream. To remove impurities such as peptides and pigments which are below this threshold but still larger than the target oligosaccharide, the first nanofiltration step could be performed using a MWCO that allows the oligosaccharide to pass into the permeate while HMW impurities remain in the retentate.

To separate the most of desired oligosaccharide from HMW impurities and to increase the yield of the desired oligosaccharide, the process should run until >70%, preferably >80%, more preferably >90% of the product passes though the membrane. Additionally, a diafiltration step could be included to increase the yield of the oligosaccharide in the clarified process stream.

After this first nanofiltration step, the only impurities in the process stream containing the oligosaccharide of interest should be the same molecular weight or lower than the oligosaccharide, and could comprise monovalent ions, divalent ions, amino acids, organic acids, monosaccharides and/or oligosaccharides.

Membranes suitable for the first nanofiltration step include polyamide or polypiperazine thin-film composite membrane materials achieving size exclusion in the range 400-1,200 Da. Examples include HYDRACoRe70 (MWCO=720 Da) or HYDRACoRe50 (MWCO=1,000 Da) membranes, both from Hydranautics (Oceanside, USA), NADIR® NP010P (MWCO=1,000-1,500 Da) or NADIR® NP030P (MWCO=500-1,000 Da) membranes (Microdyn-Nadir GmbH). Such membranes allow high flux. Additional examples of suitable membranes for nanofiltration include Trisep® SBNF (MWCO=2000 Da), a cellulose acetate nanofiltration membrane (Microdyn-Nadir GmbH) and GE-Series membranes (MWCO=1000 Da) from Suez Water Technologies & Solutions (Ratingen, Germany).

In an additional and/or alternative embodiment, the first nanofiltration step achieves the following parameters:

i) the post-filtration recovery of the oligosaccharide of interest should be >70%, preferably >80%, more preferably >90%.
ii) the concentration of the oligosaccharide of interest in the process stream should be <50% (w/v), preferably <40% (w/v), more preferably <30% (w/v), preferably <20% (w/v), more preferably <10% (w/v).
iii) the step should be carried out at a temperature of <80° C., preferably <50° C., more preferably 4-40° C. (specifically relevant for nanofiltration).
iv) the step should be carried out at a pressure of 5-50 bar, preferably at a pressure of 10-40 bar, more preferably at a pressure of 15-30 bar.

In the preferred embodiment of the method, the process stream containing the oligosaccharide of interest is concentrated and desalted after the first nanofiltration step, by applying a second nanofiltration step. The oligosaccharide of interest can also be concentrated by vacuum evaporation (e.g. using a falling-film evaporator or a plate evaporator) or reverse osmosis. The disadvantage of both these techniques is that the process stream is concentrated but not desalted. Nanofiltration is therefore the preferred method, because it can achieve simultaneous concentration and desalting, for example by using a membrane with a size exclusion limit of <2 nm.

The method for purifying the oligosaccharide of interest comprises a step in which the clarified process stream from the first nanofiltration step is subjected to at least one additional nanofiltration step to remove salt, smaller molecules and water. Preferably, the eluate from the first nanofiltration (=filtrate or permeate) is subjected directly to a second nanofiltration step to remove salts and smaller molecules from the clarified process stream.

Membranes suitable for the first nanofiltration step include polyamide or polypiperazine thin-film composite membrane materials achieving size exclusion in the range 150-300 Da, such as Filmtec™ NF270 (Dow Chemical Company, Midland, USA) and Trisep® XN45 or TS40 membranes (Microdyn Nadir GmbH). Such membranes allow a high flux. Additional examples include Trisep® 4040-XN45-TSF (Microdyn-Nadir GmbH) or GE4040F30 and GH4040F50 membranes (Suez Water Technologies & Solutions).

Nanofiltration efficiently removes significant quantities of salts and LMW impurities from the process stream containing the oligosaccharide of interest prior to electrodialysis. Nanofiltration also efficiently removes LMW contaminants after the ultrafiltration step, wherein the removal of such contaminants is beneficial for concentrating and demineralizing the solution of the oligosaccharide of interest. The use of nanofiltration to concentrate the oligosaccharide of interest results in lower energy and processing costs, and better product quality due to the more limited thermal exposure.

The method concentrates the oligosaccharide of interest from aqueous solutions, wherein the concentration of the oligosaccharide of interest in the aqueous solution is ≤20%, ≤10% or ≤5% prior to concentration.

In an additional and/or alternative embodiment, concentration by nanofiltration should achieve the following parameters:

i) an oligosaccharide concentration of >100 g/L, preferably >200 g/L, more preferably >300 g/L, most preferably >400 g/L;
ii) the amount of salt in the purified solution should be <10% %-wt, preferably <5%, more preferably <2%; and/or the conductivity should be 0.5-10.0 mS/cm$^2$, preferably 1-8 mS/cm$^2$, more preferably 1.5-4.0 mS/cm$^2$.
iii) the step should be carried out at a temperature of <80° C., preferably <50° C., more preferably 4-40° C. (specifically relevant for nanofiltration).
iv) the step should be carried out at a pressure of 5-50 bar, preferably at a pressure of 10-40 bar, more preferably at a pressure of 15-30 bar.

Pigments in the clarified solution and/or purified solution can be removed by treatment with activated charcoal. The advantage of removing pigments using activated charcoal is that both electrically charged and electrically uncharged (neutral) pigments can be removed.

Activated carbon, also called activated charcoal, is a form of carbon that has been processed to generate small, low-volume pores that increase the surface area available for adsorption. Typically, just 1 g of activated carbon has a surface area greater than 30.00 m$^2$ as determined by gas adsorption, due to its high degree of micro-porosity.

Colour-given impurities like Maillard products, Riboflavin and other LMW impurities tends to adsorb to the surface of charcoal particles. In contrast to the produced oligosaccharides the amount of the colour-given substances is much lower and/or shows in in most cases a hydrophobic behaviour. Caused by this fact, pigmented contaminants have a high removal rate from the process stream. Water-soluble materials such as oligosaccharides bind more weakly and can be eluted by rinsing with water, leaving the pigments adsorbed to the surface.

In an additional and/or alternative embodiment, the method for the purification of the oligosaccharide of interest further comprises at least one step in which the clarified process stream or eluate from a previous purification step is treated with activated carbon to remove pigments.

In a preferred embodiment, the active charcoal treatment should be carried out:

i) after the removal of water and salt in the second nanofiltration step; and/or
ii) after the removal of proteins by ultrafiltration or after the removal of remaining salts by electrodialysis (alternatively, a diafiltration step can be introduced).

Suitable activated charcoals for the removal of neutral oligosaccharides, pigments and other contaminants are (but not limited to) granulated activated charcoals like Norit GAC830EN (Cabot Corporation, Boston, USA) and Epibon Y 12×40 spezial (Donau Carbon, Frankfurt, Germany) or powdered activated charcoal like Norit DX1, Norit SA2 (Cabot Corporation) and Carbopal MB 4 (Donau Carbon).

Electrodialysis combines dialysis and electrolysis and can be used for the separation and concentration of ions in solutions based on their selective electromigration through a semipermeable membrane. Industrial electrodialysis applications date back to the early 1960s when this method was used for the demineralization of cheese whey for inclusion in infant formula. Further applications include the pH adjustment of beverages such as wines, grape must, apple juice and orange juice.

The desalination of brackish water for the production of drinking water and the demineralization of milk whey for infant food production are the most widespread applications of electrodialysis today. The basic principle of electrodialysis involves an electrolytic cell comprising a pair of electrodes submerged into an electrolyte for the conduction of ions, connected to a direct current generator. The electrode connected to the positive pole of the direct current generator is the anode, and the electrode connected to the negative pole is the cathode. The electrolyte solution then supports current flow, which results from the movement of negative and positive ions towards the anode and cathode, respectively. The membranes used for electrodialysis are essentially sheets of porous ion exchange resins with negative or positive charge groups, and are therefore described as cationic or anionic membranes, respectively. The ion exchange membranes usually consist of a polystyrene matrix carrying a suitable functional group (such as sulfonic acid for cationic membranes or a quaternary ammonium group for anionic membranes) cross-linked with divinylbenzene.

The electrolyte can be an aqueous solution comprising, for example, sodium chloride, sodium acetate, sodium propionate and/or or sulfamic acid. The electrolyte surrounds the cathode and anode and allows current to flow within the cell. The electrodialysis stack is then assembled in such a way that the anionic and cationic membranes are parallel as in a filter press between two electrode blocks, such that the stream undergoing ion depletion is well separated from the stream undergoing ion enrichment. The two solutions are also referred to as the diluate (undergoing ion depletion) and concentrate (undergoing ion enrichment).

The heart of the electrodialysis process is the membrane stack, which consists of several anion exchange and cation exchange membranes separated by spacers, installed between two electrodes. By applying a direct current, anions and cations will migrate across the membranes towards the electrodes generating a (desalted) diluate stream and a concentrate stream.

The pore size of ion exchange membranes used for electrodialysis is small enough to prevent the diffusion of the product from the diluate stream into the concentrate stream, driven by high concentration differences between the two streams.

Electrodialysis is used to remove the ions from aqueous solutions while the neutral and acidic oligosaccharides remain in the process stream. An important advantage of electrodialysis is that recombinant DNA molecules can be completely removed from the solution comprising the oligosaccharide of interest. Furthermore, the amount of salt in the process stream can be significantly reduced by electrodialysis. Indeed, sodium chloride can be completely removed from the product stream. This has the advantage that a solution containing the oligosaccharide of interest can be provided that is devoid of salts like sodium chloride, preventing any negative influence of that salt in the final product, e.g. infant food.

After nanofiltration and activated carbon treatment, most of the salt and smaller organic impurities like organic acids should be removed from the process stream. To ensure the effective removal of remaining salts and small, charged organic substances, an electrodialysis step is carried out.

Electrodialysis can be performed until the process stream reaches a stable conductivity of 0.05-1.0 mS/cm$^2$, preferably 0.1-0.5 mS/cm$^2$, more preferably 0.2-0.4 mS/cm$^2$. Furthermore, electrodialysis can be performed until the concentration of salt falls to <10.0 g/L, preferably <5.0 g/L, more preferably <1.0 g/L, most preferably <0.2 g/L.

For neutral oligosaccharides, the electrodialysis step should be run under acidic or neutral pH conditions, preferably pH 3-8, more preferably pH 4-7. For acidic oligosaccharides, the electrodialysis step should be run under neutral pH conditions, preferably pH 6-8, more preferably pH 6.5-7.5 due to the instability of acidic oligosaccharides under acidic conditions. The pH of the acidic oligosaccharide solution must be controlled during electrodialysis and adjusted with NaOH if necessary.

A reverse osmosis step can be used instead of nanofiltration for the concentration of the oligosaccharide of interest. Reverse osmosis is a membrane filtration method that concentrates particles larger than 0.1 nm in the process stream retentate while removing water. Reverse osmosis therefore concentrates the process stream but does not achieve desalination.

The method can concentrate the oligosaccharide of interest in an aqueous or organic solvent, wherein the concentration of the oligosaccharide of interest is ≤20% (w/v), ≤10% (w/v) or ≤5% (w/v) prior to the concentration.

In an additional and/or alternative embodiment, the concentration step should achieve the following parameters:

i) an oligosaccharide concentration of >300 g/L, preferably >400 g/L, more preferably >500 g/L, most preferably 600 g/L.
ii) the step should be carried out at a temperature of <80° C., preferably <50° C., more preferably 4-40° C. (specifically relevant for reverse osmosis).
iii) the step should be carried out at a pressure of 5-50 bar, preferably at a pressure of 10-40 bar, more preferably at a pressure of 15-30 bar.

In additional and/or alternative embodiment of the process, the solution containing the neutral and acidic HMO is concentrated by vacuum evaporation (e.g. using a rotary evaporator or plate evaporator) and should achieve the following parameters:

i) an oligosaccharide concentration of >300 g/L, preferably >400 g/L, more preferably >500 g/L, most preferably >600 g/L.
ii) the step should be carried out at a temperature of <80° C., preferably <50° C., more preferably 20-50° C., even more preferably 30-45° C., most preferably 35-45° C. (specifically relevant for vacuum evaporation).

To remove any potential microbial contaminants and endotoxins, the concentrated oligosaccharide of interest is filter sterilized by passage through an ultrafiltration membrane.

In a preferred embodiment of the invention, the purified oligosaccharide solution is passed through a 10 kDa filter module, such as a 5 kDa or 3 kDa MWCO filter. Suitable ultrafiltration membranes for endotoxin removal have a MWCO of at least 10 kDa, preferably at least 5 kDa, and could be spiral-wound or hollow-fibre ultrafiltration membranes. Examples of spiral-wound membranes include the SPIRA-CEL® DS UP010 (MWCO=10 kDa) or DS UP005 (MWCO=5 kDa) membranes (Microdyn-Nadir GmbH) and the Dairy-Pro® HpHT UF-5K (MWCO=5 kDa) from Koch Membranes Systems. Examples of hollow-fibre modules include the ROMICON® HF UF Cartridge PM5 (MWCO=5 kDa) from Koch Membranes Systems or Microzoa™ series membranes (MWCO=3 or 6) from Pall Cooperation (Port Washington, USA).

In a preferred embodiment, the purified oligosaccharide solution is spray dried after filter sterilization. The solution can be spray-dried using hot air to remove preferably at least 85%-wt., or more preferably at least 90%-wt. of the water. The solution can be spray-dried using any conventional spray-drying system, preferably with a fluid bed dryer attachment.

The purified solution may be spray dried to achieve a oligosaccharide of interest concentration of 5-60%-wt., preferably 10-50%-wt., more preferably 15-45%-wt. The inlet temperature can be held within the range 110-150° C., preferably 120-140° C., more preferably 125-135° C. The outlet temperature can be held within the range 60-80° C., preferably 65-70° C.

After spray drying, the purified oligosaccharide of interest can have the following properties:

i) a solid granule form; and/or
ii) a glass transition temperature of 60-90° C., preferably 62-88° C., more preferably 64-86° C., as determined by differential scanning calorimetry; and/or
iii) a particle size of 5-500 μm, preferably 10-300 μm, determined by laser diffraction; and/or
iv) a mean particle size of 10-100 μm, preferably 20-90 μm, more preferably 30-80 μm, most preferably 40-70 μm, determined by laser diffraction; and/or
v) an amorphous state, preferably an amorphous state with no characteristic peaks of crystalline matter observed by X-ray powder diffraction; and/or
vi) a moisture content of ≤10%-wt., preferably ≤8%-wt, more preferably ≤5%-wt.

The purified oligosaccharide of interest may be used for nutritional applications, preferably medical or dairy nutrition (e.g. cereal products), and more preferably infant nutrition or in medicine, preferably in prophylaxis or for the treatment of gastrointestinal disorders.

In an embodiment, the oligosaccharide of interest is a neutral oligosaccharide or a sialylated oligosaccharide, preferably a human milk oligosaccharide. The oligosaccharide of interest can be a neutral HMO or a sialylated HMO. In an additional and/or alternative embodiment, the oligosaccharide of interest is selected from the group of human milk oligosaccharides consisting of 2'-fucosyllactose, 3-fucosyllactose, 2', 3-difucosyllactose, lacto-N-triose II, lacto-N-tetraose, lacto-N-neotetraose, lacto-N-fucopentaose I, lacto-N-neofucopentaose, lacto-N-fucopentaose II, lacto-N-fucopentaose III, lacto-N-fucopentaose V, lacto-N-neofucopentaose V, lacto-N-difucohexaose I, lacto-N-difucohexaose 11, 6'-galactosyllactose, 3'-galactosyllactose, lacto-N-hexaose and lacto-N-neohexaose 3'-sialyllactose, 6'-sialyllactose, sialyllacto-N-tetraose a, sialyllacto-N-tetraose b, sialyllacto-N-tetraose c, 3-fucosyl-sialyllactose, disialyl-lacto-N-tetraose and fucosyl-LST b. The present invention will be described with respect to particular embodiments and with reference to drawings, but the invention is not limited thereto but only by the claims. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method.

Furthermore, an element described herein of an apparatus embodiment is an example of a means for carrying out the function performed by the element for the purpose of carrying out the invention.

In the description and drawings provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

Example 1: Purification of 3-fucosyllactose from Bacterial Fermentation

The HMO 3-fucosyllactose was produced by a bacterial fermentation and bacteria were removed from the fermentation broth by filtration. For removal of the bacterial cells, the fermentation broth was filtered by microfiltration using a polyethersulfone membrane having a nominal pore size of 0.05 μm (NADIR® MP005; Microdyn-Nadir, Wiesbaden), and subsequent ultrafiltration using a hollow fiber module (ULTRADYN FS-10-FS FUS-1582, 150 kDa MWCO; Microdyn-Nadir, Wiesbaden, Germany).

The cell-free broth was then processed by diafiltration with a nanofiltration step to remove salts and smaller molecules, increasing the purity of the 3-FL. A reverse osmosis system type RO40404 (Aqmos GmbH, Rodgau, Germany) was equipped with Filmtec™ NF270 nanofiltration modules. The inlet pressure was set to 8 bar and the solution was processed three times with an equal volume of reverse osmosis water in order to increase the concentration by halving the starting volume. The 3-FL solution was then passed through a FS-10-FS FUS018110 kDa hollow-fibre nanofiltration module (Microdyn-Nadir) to remove proteins and peptides.

Ions similar in size to 3-FL were removed from the process stream by electrodialysis using a PCCell P15 system (PCCell GmbH, Heusweiler, Germany) equipped with a PCCell ED 1000A membrane stack comprising a CEM: PCSK cation exchange membrane and a CEM:PcAcid60 anion exchange membrane with a size exclusion limit of 60 Da. The conductivity of the starting solutions was between 8 and 11 $mS/cm^2$ and electrodialysis continued until the conductivity fell to 0.5 $mS/cm^2$.

The 3-FL solution was then treated with activated carbon powder to remove pigments. The solution was stirred for 2 h with Norit DX1 activated charcoal, and the latter was then removed by filtration.

Another round of electrodialysis was carried out using the same setup as described above. The conductivity of the starting solution was 1.0-1.5 $mS/cm^2$ and electrodialysis continued until the conductivity fell to 0.3 $mS/cm^2$.

After electrodialysis, the 3-FL solution was concentrated by reverse osmosis using an Emrich EMRO 1.8 reverse osmosis system (Emrich Edelstahlbau, Polch, Germany) equipped with a CSM RE8040BE reverse osmosis module. The solution was concentrated until the flow rate of the filtration system dropped below 50 L/h. The dry matter after concentration was 20-25%-wt. For spray drying (see Example 2), the 3-FL solution was further concentrated using a Hei-VAP industrial evaporator (Heidolph Instruments GmbH, Schwabach, Germany) to 45%-wt. dry matter. The highly-concentrated 3-FL solution was filter-sterilized to remove endotoxins by passing it through a 5 kDa Spira-Cell WY UP005 2440 C ultrafiltration membrane (Microdyn-Nadir).

Figure 6:
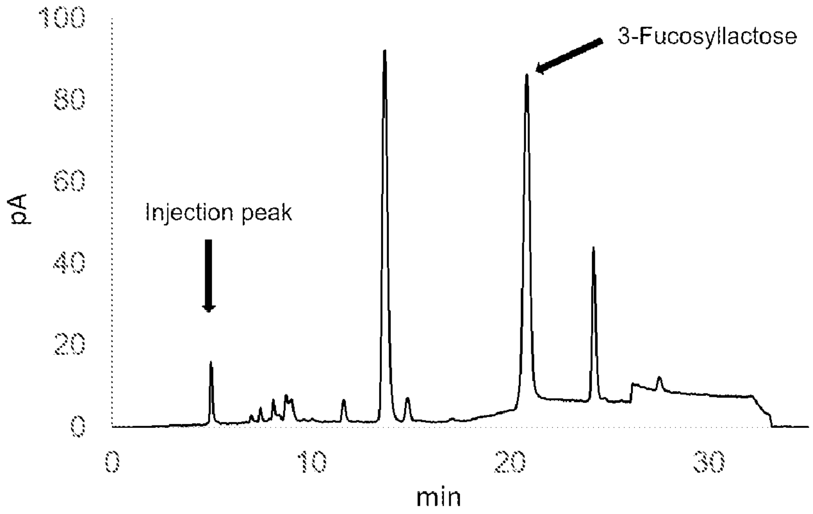
FIG. 6 shows a HPLC chromatogram of a clarified fermentation broth containing 3-fucosyllactose.
Figure 7:
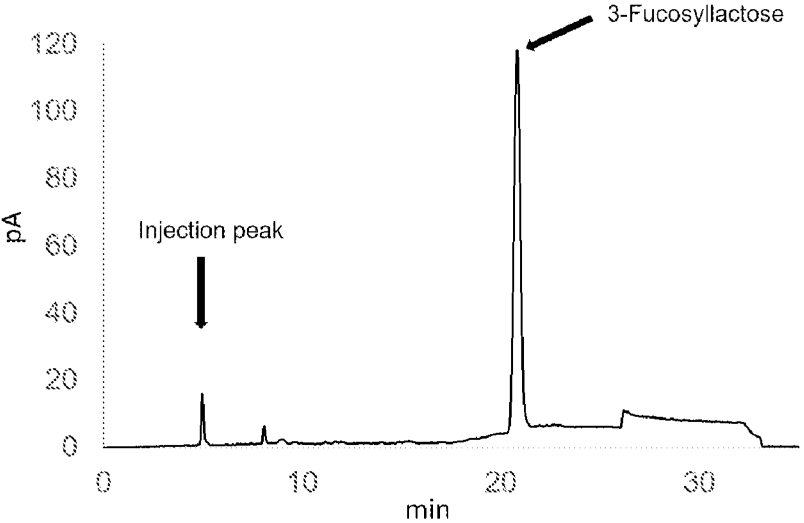
FIG. 7 shows a HPLC chromatogram of 3-fucosyllactose after purification from a fermentation broth by an exemplary embodiment of a method according to the invention.

HPLC chromatograms illustrating the purification of 3-fucosyllactose from a clarified fermentation broth by the method are displayed in FIG. 6 and FIG. 7. FIG. 6 shows a HPLC chromatogram of a clarified fermentation broth, whereas FIG. 7 shows a HPLC chromatogram of a sterile filtered process stream obtained from the clarified fermentation broth leading to the HPLC chromatogram shown in FIG. 6. Comparing of these chromatograms reveals that most of the peaks in the HPLC chromatogram (each peak represents at least one compound) of the clarified fermentation broth are absent in the HPLC chromatogram of the sterile filtered process stream.

Example 2: Obtaining 3-Fucosyllactose in Solid Form by Spray Drying

The 3-FL solution obtained by filtration and electrodialysis was concentrated 45% wt. and filter sterilized to remove any bioburden and endotoxins as described in Example 1. The highly-concentrated and sterile 3-FL solution was then spray dried using an LTC-GMP spray dryer (Nubilosa, Konstanz, Germany). The 45%-wt. 3-FL solution was passed through the spray dryer nozzles at 130° C. and 3.5 bar, and the flow was adjusted to maintain an exhaust temperature of 66-67° C. Using these settings, a spray dried powder containing less than 5% moisture was obtained. The moisture content was determined by Karl-Fischer titration.

The invention claimed is:

1. A method for purification of an oligosaccharide of interest from a fermentation broth, wherein the method comprises:

(i) providing a fermentation broth which comprises the oligosaccharide of interest, biomass, microbial cells and carbohydrates other than the oligosaccharide of interest;

(ii) removing the microbial cells from the fermentation broth, thereby providing a process stream;

(iii) subjecting the process stream to a first filtration using a nanofiltration membrane, thereby providing a filtrate which contains the oligosaccharide of interest, wherein the nanofiltration membrane used in the first filtration has a molecular weight cut-off of between about 700 Dalton and about 3,000 Dalton;

(iv) subjecting the filtrate to a second filtration using a nanofiltration membrane, thereby providing a retentate which contains the oligosaccharide of interest, wherein the nanofiltration membrane used in the second filtration has a molecular weight cut-off between 100 Dalton and 1,000 Dalton; and (v) removing one or more salts from the process stream using electrodialysis thereby providing a purified preparation of the oligosaccharide of interest wherein the method does not comprise an ion exchange step.

2. The method according to claim 1, wherein the microbial cells are removed from the fermentation broth by subjecting the fermentation broth to at least one centrifugation and/or to at least one filtration.

3. The method according to claim 2, wherein the at least one filtration is a microfiltration.

4. The method according to claim 3, wherein the process stream is subjected to at least one ultrafiltration, using a membrane having a molecular weight cut-off of about 50 kDa.

5. The method according to claim 1, wherein the nanofiltration membrane used in the first filtration has a molecular weight cut-off of about 1,000 and about 2,000 Dalton.

6. The method according to claim 1, wherein the nanofiltration membrane used in the second filtration has a molecular weight cut-off of about 150 Dalton and about 500 Dalton.

7. The method according to claim 1, wherein the oligosaccharide of interest is a HMO selected from the group consisting of 2'-fucosyllactose, 3-fucosyllactose, 2', 3-difucosyllactose, lacto-N-triose II, lacto-N-tetraose, lacto-N-neotetraose, lacto-N-fucopentaose I, lacto-N-neofucopentaose, lacto-N-fucopentaose II, lacto-N-fucopentaose III, lacto-N-fucopentaose V, lacto-N-neofucopentaose V, lacto-N-difucohexaose I, lacto-N-difucohexaose II, 6'-galactosyllactose, 3'-galactosyllactose, lacto-N-hexaose and lacto-N-neohexaose 3'-sialyllactose, 6'-sialyllactose, sialyllacto-N-tetraose a, sialyllacto-N-tetraose b, sialyllacto-N-tetraose c, 3-fucosyl-sialyllactose, disialyl-lacto-N-tetraose and fucosyl-LST b, or any other HMO as listed in Table 1.

8. The method according to claim 1, wherein the process stream is subjected to the second filtration such that i) the amount of salt in the retentate is <10%-wt., and/or ii) the conductivity is between 0.5 and 10.0 $mS/cm^2$.

9. The method according to claim 1, wherein the process stream is subjected to a concentration.

10. The method according to claim 9, wherein the concentration is performed by nanofiltration at a temperature of <80° C.; and/or by reverse osmosis at a temperature of 20° C. to 50° C.; and/or at a pressure between >5 bar and <50 bar.

11. The method according to claim 1, wherein the process stream is subjected to a concentration such that the concentration of the oligosaccharide of interest is ≥100 g/L.

12. The method according to claim 1, wherein the process stream is subjected to removal of one or more colorants.

13. The method according to claim 12, wherein the removing of colorants is performed i) before or after diafiltration;

ii) before or after concentrating the process stream; and/or iii) before or after electrodialysis.

14. The method according to claim 1, wherein the electrodialysis is an electrodialysis under neutral conditions or an electrodialysis under acidic conditions.

15. The method according to claim 1, wherein the process stream after removal of one or more salts contained therein i) comprises an amount of salt that is <1%-wt.; and/or ii) has a conductivity of between 0.05 and 1.0 $mS/cm^2$.

16. The method according to claim 1, wherein the process stream is spray-dried, preferably optionally spray dried i) at an inlet temperature in the range of 110-150° C. and an outlet temperature in the range of 60-80° C.; and/or ii) at a concentration of the oligosaccharide of interest in the process stream of 5-60%-wt.

17. The method according to claim 1, wherein the purity of the oligosaccharide of interest in the purified preparation is ≥80%-wt., with respect to dry matter of the purified preparation.

18. The method according to claim 3, wherein the microfiltration comprises using a membrane which has a molecular weight cut-off of about 500 kDa.

19. The method according to claim 3, wherein the microfiltration comprises using a membrane which has a molecular weight cut-off of about 150 kDa.

20. The method according to claim 3, wherein the process stream is subjected to at least one ultrafiltration, using a membrane having a molecular weight cut-off of about 30 kDa.

* * * * *